US00RE39694E

(19) United States
(12) Reissued Patent
Choke-arpornchai et al.

(10) Patent Number: US RE39,694 E
(45) Date of Reissued Patent: Jun. 19, 2007

(54) VOLATILE ACTIVES DISPENSER

(75) Inventors: Bunchorn Choke-arpornchai, Samutprakarn (TH); Nittayanun Korprasert, Bangkok (TH); Chadaporn Kusumarn, Bangkok (TH)

(73) Assignee: S.C. Johnson & Son, Inc., Racine, WI (US)

(21) Appl. No.: 29/256,634

(22) Filed: Mar. 22, 2006

Related U.S. Patent Documents

Reissue of:
(64) Patent No.: Des. 487,144
Issued: Feb. 24, 2004
Appl. No.: 29/168,588
Filed: Oct. 4, 2002

(51) LOC (8) Cl. ..... 23-04
(52) U.S. Cl. ..... D23/366
(58) Field of Classification Search ..... D23/366–369; 239/52, 53, 57–59, 34, 60; 261/DIG. 65; 422/305, 120; 454/157, 156
See application file for complete search history.

(56) References Cited

U.S. PATENT DOCUMENTS

D403,420 S * 12/1998 Vullion ..... D23/367
D419,659 S * 1/2000 Yang ..... D23/366
D422,350 S * 4/2000 Wu ..... D23/367

* cited by examiner

*Primary Examiner*—Lisa Lichtenstein

(57) CLAIM

The ornamental design for the volatile actives dispenser, as shown and described.

DESCRIPTION

FIG. 1 is a front perspective view from above and to one side of the volatile actives dispenser showing the new design.
FIG. 2 is a front view of the volatile actives dispenser of FIG. 1.
FIG. 3 is a rear view of the volatile actives dispenser of FIG. 1.
FIG. 4 is a right side view of the volatile actives dispenser of FIG. 1.
FIG. 5 is a left side view of the volatile actives dispenser of FIG. 1.
FIG. 6 is a top plan view of the volatile actives dispenser of FIG. 1; and,
FIG. 7 is a bottom plan view of the volatile actives dispenser of FIG. 1.

1 Claim, 2 Drawing Sheets

Figure 1:
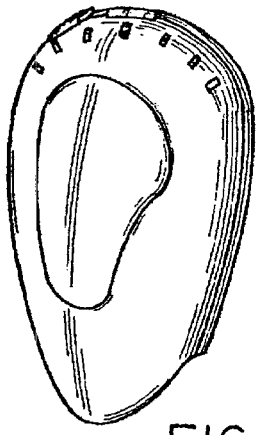
Figure 2:
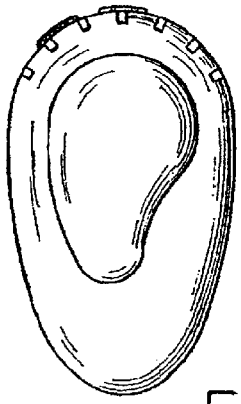
Figure 3:
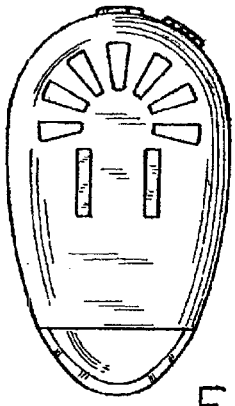
Figure 4:
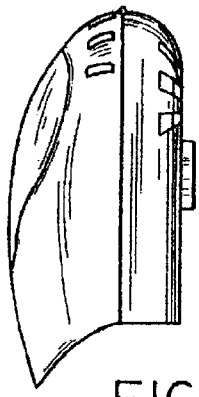
Figure 5:
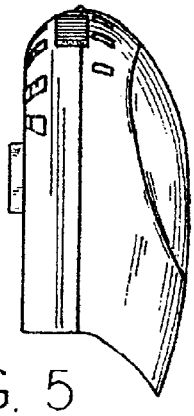
Figure 6:
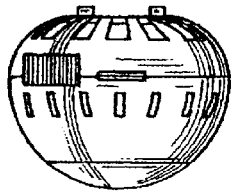
Figure 7:
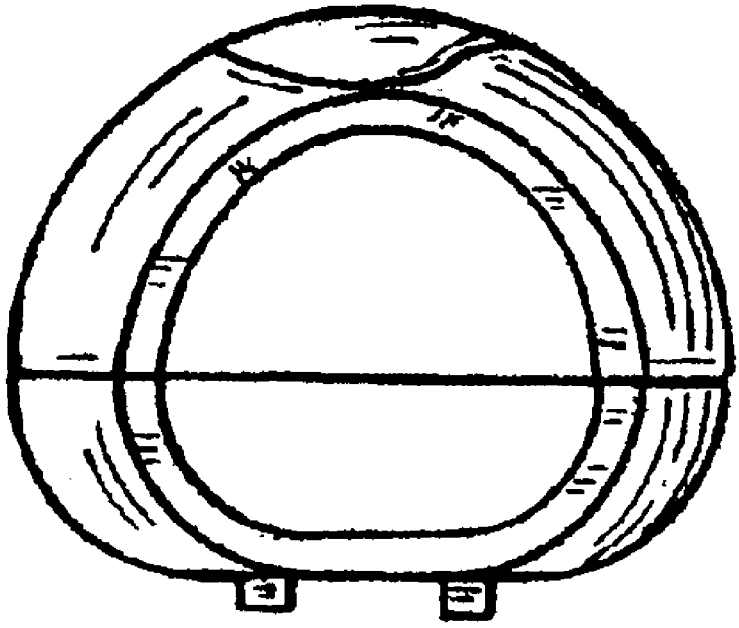

Matter enclosed in heavy brackets [ ] appears in the original patent, but forms no part of this reissue; matter printed in italics indicates the additions made by reissue.